US010259857B2

(12) United States Patent
Masland

(10) Patent No.: US 10,259,857 B2
(45) Date of Patent: *Apr. 16, 2019

(54) METHOD FOR AUGMENTING VISION IN PERSONS SUFFERING FROM PHOTORECEPTOR CELL DEGENERATION

(71) Applicant: THE GENERAL HOSPITAL CORPORATION, Boston, MA (US)

(72) Inventor: Richard H. Masland, Weston, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/875,174

(22) Filed: Oct. 5, 2015

(65) Prior Publication Data
US 2016/0022841 A1   Jan. 28, 2016

Related U.S. Application Data

(60) Division of application No. 11/036,629, filed on Jan. 13, 2005, now Pat. No. 9,434,781, which is a continuation of application No. PCT/US03/22565, filed on Jul. 18, 2003.

(60) Provisional application No. 60/397,088, filed on Jul. 18, 2002.

(51) Int. Cl.
A61K 48/00 (2006.01)
C12N 15/86 (2006.01)
C12N 15/63 (2006.01)
C07K 14/705 (2006.01)
A61K 9/00 (2006.01)
A61K 38/17 (2006.01)
C12N 7/00 (2006.01)
A01K 67/00 (2006.01)

(52) U.S. Cl.
CPC .......... C07K 14/705 (2013.01); A61K 9/0048 (2013.01); A61K 38/177 (2013.01); A61K 48/0075 (2013.01); C12N 7/00 (2013.01); A01K 2217/05 (2013.01); A01K 2267/03 (2013.01); A61K 48/00 (2013.01); C12N 2710/10043 (2013.01); C12N 2710/10071 (2013.01); C12N 2710/16043 (2013.01); C12N 2710/16071 (2013.01); C12N 2710/16243 (2013.01); C12N 2710/16271 (2013.01); C12N 2710/22043 (2013.01); C12N 2710/22071 (2013.01); C12N 2710/24043 (2013.01); C12N 2710/24071 (2013.01); C12N 2740/10043 (2013.01); C12N 2740/10071 (2013.01); C12N 2740/15043 (2013.01); C12N 2740/15071 (2013.01); C12N 2799/021 (2013.01); C12N 2799/04 (2013.01); C12N 2830/008 (2013.01)

(58) Field of Classification Search
CPC .. C07K 14/705; A61K 48/00; A61K 48/0075; C12N 2799/021; C12N 2799/04; C12N 2830/008
See application file for complete search history.

(56) References Cited

U.S. PATENT DOCUMENTS

| 4,454,170 A * | 6/1984 | Goepfert ........... B32B 17/10339 |
| | | 156/99 |
| 4,498,919 A | 2/1985 | Mann |
| 5,944,747 A | 8/1999 | Greenberg et al. |
| 6,204,251 B1 | 3/2001 | Cuthbertson |
| 6,610,287 B1 | 8/2003 | Breakerfield et al. |
| 7,090,864 B2 | 8/2006 | Pardridge |
| 7,144,733 B2 | 12/2006 | Miesenbock et al. |
| 2002/0193327 A1 | 12/2002 | Nemerow et al. |
| 2007/0261127 A1 | 11/2007 | Boyden et al. |

FOREIGN PATENT DOCUMENTS

| WO | 2004009022 A2 | 1/2004 |
| WO | 2007131180 A2 | 11/2007 |
| WO | 2008022772 A1 | 2/2008 |

OTHER PUBLICATIONS

Oberdick J et al. A promoter that drives transgene expression in Cerebellar Purkinje and Retinal Bipolar Neurons. Science 248:223-226, 1990.*
Liang et al. Long-term protection of retinal structure but not function using RAAV.CNTF in animal models of retinitis pigmentosa. Mol. Ther. 4:461-472, 2001.*
Acland et al., "Gene therapy restores vision in a canine model of childhood blindness", Nat. Genet. 28(1):92-95 (2001).
Alexander et al., "Restoration of cone vision in a mouse model of achromatopsia", Nat. Med. 13(6):685-687 (2007).
Bainbridge et al., "Effect of gene therapy on visual function in Leiber's congenital amaurosis", N. Engl. J. Med. 358(21):2231-2239 (2008).

(Continued)

Primary Examiner — Quang Nguyen
(74) Attorney, Agent, or Firm — Nixon Peabody LLP; David S. Resnick; Teresa A. Ptashka

(57) ABSTRACT

The invention provides compositions and methods of treating subjects afflicted with a photoreceptor disorder. Methods for treating a subject suffering from a disorder characterized by photoreceptor cell degeneration are provided, wherein a gene encoding a photosensitive protein is introduced into a retinal cell of a subject. In one aspect of the invention, the retinal cells which receive the photosensitive protein include non-photoreceptor cells such as horizontal cells, amacrine cells, bipolar cells, and ganglion cells.

5 Claims, No Drawings

(56) References Cited

OTHER PUBLICATIONS

Bennett et al., "Gene therapy for ocular disease" Mol. Ther. (6):501-505 (2000).
Berson "Phototransduction in ganglion-cell photoreceptors", Pflugers Arch. 454(5):849-855 (2007).
Bi et al., "Ectopic expression of a microbial-type rhodopsin restores visual responses in mice with photoreceptor degeneration", Neuron. 50(1).23-33 (2006).
Borras, "Recent developments in ocular gene therapy", Exp Eye Res. 76(6):643-652 (2003).
Campochiaro et al., "Gene therapy for retinal and choridal diseases", Expert Opin. Biol. Ther. 2(5):537-544 (2002).
Cheng et al., "TrkB gene transfer protects retinal ganglion cells from axotomy-induced death in vivo", J. Neurosci. 22(10):3977-3986 (2002).
Hankins et al., "Melanopsin: an exciting photopigment", Trends Neurosci. 31(1):27-36 (2008). Epub Dec. 4, 2007.
Hauswirth et al., "Ocular gene therapy: quo vadis" Invest. Ophthalmal. Vis. Sci. 41(10):2821-2826 (2000).
Hossain et al., "Artificial means for restoring vision", BMJ. 330(7481):30-33 (2005).
Ivanova et al., "Evaluation of the adeno-associated virus mediated long-term expression of channelrhodopsin-2 in the mouse retina", Mol. Vis. 15:1680-1689 (2009).
Johnson et al., "Brain derived neurotrophic factor supports the survival of cultured rat retinal ganglion cells", J. Neurosci. 6:3031-3038 (1986).
Lagali et al., "Light-activated channels targeted to ON bipolar cells restore visual function in retinal degeneraton", Nat. Neurosci. 11(6):667-675 (2008).
Lanyi, "Halorhodopsin, a light-driven electrogenic chloride-transport system", Physiol. Rev. 70(2):319-330 (1990).
Maguire et al., "Safety and efficacy of gene transfer for Leber's congenital amaurosis", N. Engl. J. Med., 358(21):2240-2248 (2008).
Mancuso et al., "Colorblindness Cure; Gene Therapy Confers a New Sensation", Abstract, ARVO Meeting (Apr. 2008).
Mcfarland et al., "Gene therapy for proliferative ocular diseases", Expert Opin. Biol. Ther. 4(7):1053-1058 (2004).
Mckinnon et al., "Baculoviral IAP repeat-containing-4 protects optic nerve axons in a rat glaucoma model", Mol. Ther.5(6):780-787 (2002).
Medeiros et al., "Preservation of ganglion cell layer neurons in age-related macular degeneration", Invest. Ophthalmol. Vis. Sci. 42(3):795-803 (2001).
Melyan et al., "Addition of human melanopsin renders mammalian cells photoresponsive", Nature 433 (7027):741-745 (2005).
Mori et al., "AAV-mediated gene transfer of pigment epithelium-derived factor inhibits choroidal neovascularization", Invest. Opththalmol. Vis. Sci. 43(6):1994-2000 (2002).
Muneyuki et al., "Time-resolved measurements of photovoltage generation by bacteriorhodopsin and halorhodopsin adsorbed on a thin polymer film", J. Biochem. 125(2):270-276 (1999).
Nagel et al., "Channelrhodopsin-1: a light-gated proton channel in green algae", Science 296(5577):2395-2398 (2002).
Pan et al., "Functional Expression of a Directly light-Gated membrane Channel in Mammalian Retinal Neurons: A Potential Strategy for Restoring Light Sensitivity to the Retina after Photoreceptor Degeneration", Abstract, ARVO annual meeting (2005).
Panda et al., "Illumination of the melanopsin signaling pathway", Science 307(5709):600-604 (2005).
Qiu et al., "Induction of photosensitivity by heterologous expression of melanopsin", Nature 433(7027): 745-749 (2005).
Raisler et al., "Adeno-associated virus type-2 expression of pigmented epithelium-derived factor or Kringles 1-3 of angiostatin reduce retinal neovascularization", Proc. Natl. Acad. Sci. U.S.A. 99(13):8909-8914 (2002).
Sakamoto et al., "Gene targeting to the retina", Adv. Drug Deliv. Rev. 52(1):93-102 (2001).
Shastry "Hereditary degenerative retinopathies: optimism for somatic gene therapy" IUBMB Life 49(6):479-484 (2000).
Strettoi et al., "Modifications of retinal neurons in a mouse model of retinitis pigmentosa", Proc. Natl. Acad. Sci. U. S.A. 97(20 ): 11020-11025 (2000).
Surace et al., "Adeno-associated viral vectors for retinal gene transfer", Prog. Retin. Eye Res. 22(6):705-719 (2003).
Tan et al., "The relationship between opsin overexpression and photoreceptor degeneration", Invest. Ophthalmol. Vis. Sci. 42(3):589-600 (2001).
Wong et al., "Photoreceptor adaptation in intrinsically photosensitive retinal ganglion cells", Neuron. 48(6):1001-1010 (2005).
Zemelman et al., "Selective Photostimulation of Genetically ChARGed Neurons", Neuron 33(1):15-22 (2002).

\* cited by examiner

METHOD FOR AUGMENTING VISION IN PERSONS SUFFERING FROM PHOTORECEPTOR CELL DEGENERATION

CROSS REFERENCE TO RELATED APPLICATIONS

This application is a divisional application which claims the benefit of U.S. Utility application Ser. No. 11/036,629 filed Jan. 13, 2005, which is a continuation of International Patent Application No. PCT/US03/22565 filed Jul. 18, 2003, which claims the benefit under 35 U.S.C. § 119(e) of U.S. Provisional Application No. 60/397,088 filed Jul. 18, 2002, the contents of each of which are incorporated herein by reference in their entireties.

BACKGROUND OF THE INVENTION

The two major causes of retinal photoreceptor cell degeneration are age-related macular degeneration (ARMD) and retinitis pigmentosa. ARMD usually occurs in older individuals, and is characterized by a degeneration of the retinal pigment epithelium whereby photoreceptor cells of the central retina degenerate. Retinitis pigmentosa represents a group of human hereditary retinal degenerations which are named for the characteristic intraretinal pigment which appears around the mid-peripheral retina of individuals with retinitis pigmentosa (Berson, E. L. (1996) PNAS 93:4526-4528). Retinitis pigmentosa is a disorder which has been linked to a number of different genes. The condition primarily affects the rod cells of the retina, but can eventually lead to loss of peripheral vision and blindness. Both retinitis pigmentosa and ARMD primarily involve the degeneration of retinal photoreceptor cells, while other neurons of the retina, including retinal ganglion cells whose long axons form the optic nerve, are substantially preserved.

Both ARMD and retinitis pigmentosa affect a substantial portion of the population. ARMD affects approximately 15,000,000 people in the United States. It is estimated that total blindness eventually results in 5-10% of these persons. ARMD accounts for 17% of new cases of blindness in the United States annually. Because ARMD is primarily a disease of individuals over 65 years old, the incidence of ARMD is expected to increase as the population in the United States ages. There are approximately 100,000 individuals affected with retinitis pigmentosa in the United States, which unlike ARMD, affects younger and older individuals. The number of persons diagnosed with retinitis pigmentosa who eventually progress to complete blindness is difficult to estimate, because many retinitis pigmentosa patients develop 'tunnel vision" with a small island of preserved vision. If approximately 5% of ARMD patients and 50% of retinitis pigmentosa patients become blind from their disease, an estimated total of 800,000 patients would be candidates for treatment for degenerative photoreceptor cells.

One possible method for restoring vision in patients afflicted with a photoreceptor degeneration disorder is through the use of a visual input which is capable of activating retinal ganglion cells. If activation by the visual input is successful, then varying degrees of vision should be restored. One suggested method for activating retinal ganglion cells through a visual input is with an electronic stimulator which electrically activates the retinal ganglion cells. Known as a "retina chip" or "silicon retina," an electronic stimulator is the focus of much research and development, however there remain many problems associated with the use of an electronic stimulator. For example, spatial resolution problems associated with the stimulating array may occur, as well as toxicity which often accompanies the use of a foreign object in the body. Due to these complications, use of electronic stimulators is still years away from clinical application. There thus remains a need for a treatment for patients suffering from degeneration of their retinal photoreceptor cells.

SUMMARY OF THE INVENTION

The present invention provides compositions and methods for treating subjects afflicted with a photoreceptor disorder. The present invention provides photosensitive proteins which may be introduced into retinal neurons which do not normally contain such proteins.

In one embodiment, the invention provides a method for treating a subject suffering from a disorder characterized by photoreceptor cell degeneration, e.g. retinitis pigmentosa, macular degeneration, age-related macular degeneration, and a collection of sporadic and inherited diseases, comprising the step of introducing into a retinal cell of the subject a gene encoding a photosensitive protein.

In another embodiment, the retinal cell of the subject is a non-photoreceptor cell, e.g. horizontal cells, amacrine cells, bipolar cells, and ganglion cells. In another embodiment of the invention, the gene which is introduced into the retinal cell is selected from the group consisting of rhodopsin, cryptochrome, melanopsin, pineal opsin, and bacteriorhodopsin. In another embodiment, the gene is introduced into the retinal cell of the subject via a gene therapy vector. In yet another embodiment, the gene therapy vector is a viral vector. The vector may comprise a cell-type specific promoter, e.g. L7, thy-1, recoverin, calbindin, or GAD-67, operatively-linked to the gene.

In yet another embodiment of the invention, the vision of the subject is further restored by the subject wearing photosensitive corrective lenses.

The invention also provides a method of treatment for age-related macular degeneration in a subject, comprising the steps of introducing a gene encoding a photosensitive protein into a retinal cell of the subject. In one embodiment, the retinal cell is selected from the group consisting of horizontal cells, amacrine cells, bipolar cells, and ganglion cells. In another embodiment of the invention, the retinal cell of the subject is a non-photoreceptor cell, e.g. horizontal cells, amacrine cells, bipolar cells, and ganglion cells. In yet another embodiment, the photosensitive protein is selected from the group consisting of rhodopsin, cryptochrome, melanopsin, pineal opsin, and bacteriorhodopsin. In another embodiment of the invention, the gene encoding a photosensitive protein is introduced into a retinal cell of the subject using a gene therapy vector. In a further embodiment, the gene therapy vector is a viral vector, including a viral vector which contains a cell-type specific promoter of a gene. In yet a further embodiment, the cell-type specific promoter is selected from cell-type specific promoters such as L7, thy-1, recoverin, calbindin, and GAD-67.

In another embodiment of the invention, a method of converting a non-photoreceptor neuron into a photoreceptor neuron is provided wherein a gene encoding a photosensitive protein is introduced into a non-photoreceptor cell, e.g. horizontal cells, amacrine cells, and ganglion cells. In one embodiment, the non-photoreceptor cell is a bipolar cell, wherein the conductance of the non-photoreceptor cell's ion channels is affected. In another embodiment, the photosensitive protein is selected from the group consisting of rhodopsin, cryptochrome, melanopsin, pineal opsin, and bacteriorhodopsin. In yet another embodiment of the invention, the gene encoding a photosensitive protein embodiment, the gene therapy vector is a viral vector, including a viral vector which contains a cell-type specific promoter of a gene. In yet a further embodiment, the cell-type specific promoter is selected from cell-type specific promoters such as L7, thy-1, recoverin, calbitain, and GAD-67.

DETAILED DESCRIPTION OF THE INVENTION

The present invention provides compositions and methods of restoring vision in a subject suffering from a disorder characterized by photoreceptor cell degeneration. The method comprises the steps of introducing a photosensitive or light-sensitive protein into a retinal neuron, including a non-photoreceptor neuron of the retina.

The retina is the nerve cell layer of the eye. The retina is a thin, transparent tissue containing about 120 million separate rod cells (night vision) and 7 million cone cells (day and color vision) as well as millions of other structural supporting and interconnecting cells. Photoreceptor cells consist of rods and cones, which are the photosensitive cells of the retina. The rods contain rhodopsin, the rod photopigment, and the cones contain other distinct photopigments, which respond to light and ultimately trigger a neural discharge in the output cells of the retina, the ganglion cells. Ultimately, this signal is registered as a visual stimulus in the visual cortex. The retinal pigment epithelial (RPE) cells produce, store and transport a variety of factors that are responsible for the normal function and survival of photoreceptors.

The compositions and methods of the present invention, may thus be used for treating disorders characterized by photoreceptor cell degeneration. A "disorder characterized by photoreceptor cell degeneration" is defined herein as any condition marked by a decrease in photoreceptor cell number and/or function. In one embodiment of the invention, the disorder is age-related macular degeneration. As used herein, "age-related macular degeneration" is defined as an age-related disorder which causes a decrease in visual acuity and possible loss of central vision. In another embodiment of the invention, the disorder is retinitis pigmentosa. Other retinal disorders which can result in photoreceptor cell death include edema, ischemic conditions and uveitis. Macular and retinal edema are often associated with metabolic illnesses such as diabetes mellitus. Retinal edema is found in a large percentage of individuals who have undergone cataract extraction and other surgical procedures upon the eye. Edema is also found with accelerated or malignant hypertension. Macular edema is a common complication of prolonged inflammation due to uveitis, Eales disease, or other diseases. Local edema is associated with multiple cystoid bodies ("cotton bodies") as a result of AIDS.

The terms "retinal cell" and "retinal neuron" are intended to mean a nerve or neuron cell which is a capable of becoming electrically excited and can also convey electrical impulses. As used herein, the terms retinal cell and retinal neuron are used interchangeably.

In one embodiment of the invention, photosensitive proteins are introduced into retinal neurons which are non-photoreceptor cells. The term "non photoreceptor cell" as used herein, refers to any cell of the retina which cannot respond to light. In a further embodiment of the invention, non-photoreceptor cells include, but are not limited to, horizontal cells, amacrine cells, bipolar cells, and/or ganglion cells. Horizontal cells are cells of the outer retina which are involved in signal processing and feedback to both photoreceptor and bipolar cells. Bipolar cells mediate signal between the rods and cones (photoreceptor cells) and amacrine and/or ganglion cells. Amacrine cells are found in the inner retina, and act as a bridge between the photoreceptor pathway and ganglion cells. Ganglion cells are found in the inner most region of the retina and carry the signal that originated with the photoreceptor cells through the optic fiber layer to the optic disk, which is the origin of the optic nerve. Also included in the invention are methods of targeting any of the various subtypes of these retinal cells.

The invention also provides a photosensitive protein which is introduced into a retinal cell of a subject. The terms "photosensitive protein" or "light sensitive protein" are used herein interchangeably and describe a light absorbing protein which can regenerate its photosensitivity after exposure to light. In one embodiment of the invention, a photosensitive protein includes, but is not limited to, rhodopsin, any member of the melanopsin family, the cryptochrome families, pineal opsin, and/or bacteriorhodopsin. A photosensitive protein of the invention can occur naturally in plant, animal, archaebacterial, or bacterial cells or can alternatively be created through laboratory techniques. Photosensitive proteins of the invention can be introduced separately or in combination with other photosensitive proteins, or in combination with intracellular signalling proteins.

In one embodiment of the invention, pineal opsins or melanopsin proteins are introduced into retinal cells. Photosensitive proteins selected from the class consisting of pineal opsins and melanopsins are beneficial because this class normally exists in an environment removed from the systems of the retinal pigment epithelium, which are capable of enzymatically re-isomerizing all transretinal to 11-cis retinal. One advantage of this class of opsins is that they can regenerate their sensitivity through an entirely different mechanism, independent of the retinal pigment epithelium. Melanopsin and pineal opsins are also preferred because they have been shown to exist in primate retinas.

In one embodiment of the invention, human melanopsin is used to restore vision in a subject. Human melanopsin is normally present in human retinas, and, therefore, would not be subject to immune rejection. The gene for human melanopsin has been cloned and sequenced and is available through publicly maintained databases such as NCBI PubMed (Genbank Accession No. AF147788). Human melanopsin is normally present in rare types of retinal amacrine and ganglion cells, and is part of the normal phototransductive mechanism. In another embodiment of the invention, a member of the cryptochrome family is used to restore vision in a subject. Cryptochromes are flavoproteins which are sensitive to blue light. In another embodiment, rhodopsin is used to restore vision in a subject suffering from loss of photoreceptor cells. In yet another embodiment of the invention, bacteriorhodopsin is introduced into non-photoreceptor cells in the retina of a subject suffering from vision loss due to photoreceptor degeneracy.

Many retinal non-photoreceptor neurons already contain intracellular signaling cascades, which, if activated accordingly, would lead to the restoration of vision. For example, in bipolar cells a signaling cascade pathway couples the excitation of bipolar cell synapses to a G-protein. The restoration of vision in a subject suffering from photoreceptor cell degeneration could be accomplished by introducing a molecule which is a component of a signaling cascade that is normally initiated through the activation of a light-sensitive protein. In yet another embodiment of the invention, a member of a signal transduction cascade normally found in a photosensitive protein-containing cell is introduced to retinal cells. Elements of signaling cascades that could be introduced include, but are not limited to, molecules normally found in melanopsin-containing neurons or pineal opsin-containing neurons.

In another embodiment of the invention, the vision of a subject is further restored through the use of photosensitive corrective lenses. As used herein, the term "photosensitive corrective lens" refers to any lens that can darken in the presence of light. Included in the invention are photosensitive corrective lenses which fit directly on the eyeball under the eyelids or contact lenses, and lenses which are placed in an eyeglass frame or structural support. Photosensitive corrective lenses are capable of filtering or blocking bright light to the eye of the wearer, and are made from a photosensitive material which exhibits alterable photochromic effects. The amount of light which is blocked is dependent upon the amount of ambient light entering the lens and type of photosensitive material used to make the lens. In one embodiment, photosensitive corrective lenses are used to help retinal cells which have received photosensitive proteins, adjust to light.

In one embodiment of the invention, a "nucleic acid molecule" or an "isolated nucleic acid molecule," used interchangeably herein, encoding a photosensitive protein is introduced into non-photoreceptor retinal cells of a subject afflicted with a photoreceptor degeneracy disorder. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A nucleic acid molecule used in the methods of the present invention, e.g., a nucleic acid molecule having the nucleotide sequence of encoding a photosensitive protein, can be isolated using standard molecular biology techniques. Using all or portion of the nucleic acid sequence a photosensitive protein as a hybridization probe, nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

A nucleic acid molecule encoding a photosensitive protein can also be isolated by the polymerase chain reaction (PCR) using synthetic oligonucleotide primers designed based upon the sequence of a gene encoding a photosensitive protein of interest. A nucleic acid used in the methods of the invention can be amplified using cDNA, mRNA or, alternatively, genomic DNA as a template and appropriate oligonucleotide primers according to standard PCR amplification techniques. Furthermore, oligonucleotides corresponding nucleotide sequences encoding a photosensitive protein can be prepared by standard synthetic techniques, e.g., using an automated DNA synthesizer.

The term "isolated nucleic acid molecule" includes nucleic acid molecules which are separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

In another embodiment of the invention, an isolated nucleic acid molecule encoding a photosensitive protein is operatively linked to a cell-type specific promoter. The nucleic acid encoding the photosensitive protein to be operatively linked to the promoter may be any nucleic acid sequence of interest including any RNA or DNA sequence encoding a peptide or protein of interest, for example, rhodopsin, any member of the melanopsin family, pineal opsin, bacteriorhodopsin, and a cryptochrome. In one embodiment of the invention, the cell-type specific promoter is from L7, thy-1, recoverin, calbindin, or the GAD-67 gene.

The nucleic acid sequence encoding the photosensitive protein of interest may be synthetic, naturally derived, or a combination thereof. As well, the nucleic acid sequence could be a fragment of the natural sequence, for example only include the catalytic domain or a structure of particular importance. The gene encoding the photosensitive protein of interest might encode a recombinant protein. Depending upon the nature of the nucleic acid encoding the protein of interest, it may be desirable to synthesize the sequence with mammalian preferred codons. The mammalian preferred codons may be determined from the codons of highest frequency in the proteins expressed in the largest amount in particular mammalian species of interest, and is known to one skilled in the art.

In one embodiment of the invention, a gene encoding a photosensitive protein is inserted into a vector. As used herein, the term "vector" refers to a nucleic acid molecule capable of transporting another nucleic acid to which it has been linked. The preparation of vectors may involve techniques such as restriction digestion, ligation, gel electrophoresis, DNA sequencing and PCR. A wide variety of cloning vectors are available to perform the necessary cloning steps. A variety of strategies are available for ligating fragments of DNA, the choice of which depends on the nature of the termini of the DNA fragments, such choices are readily made by the skilled artisan. Especially suitable for this purpose are the cloning vectors with a replication system that is functional in *Escherichia coli* such as pBR322, the pUC series M13mp series, pACYC184, pBluescript etc. Nucleic acid sequences may be introduced into these vectors and the vectors may be used to transform *E. coli* which may be grown in an appropriate medium. Plasmids may be recovered from the cells upon harvesting and lysing the cells. Final constructs may be introduced into vectors compatible with integration into the retina.

Some vectors may be capable of directing the expression of genes to which they are operably linked. The vector may include transcriptional promoter elements which are operably linked to the gene(s) of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

Within a recombinant vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). As used herein, the term "expression vectors" are intended to mean vectors capable of directing the expression of genes to which they are operatively linked. The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., cell-type specific regulatory sequences). It will be appreciated by those skilled in the art that the design of the vector can depend on such factors as the choice of the host cell to be transformed, the level of expression of protein desired, and the like. The vectors of the invention can be introduced into host cells to thereby produce proteins or peptides, including fusion proteins or peptides, encoded by nucleic acids encoding photosensitive proteins.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a photosensitive protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning:—A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that containing the photosensitive protein or can be introduced on a separate vector. Cells stably transfected with the introduced nucleic acid can be identified by drug selection (e.g., cells that have incorporated the selectable marker gene will survive, while the other cells die).

The host cells of the invention can also be used to produce non-human transgenic animals. For example, in one embodiment, a host cell of the invention is a fertilized oocyte or an embryonic stem cell into which a photosensitive protein coding nucleic acid sequence has been introduced. Such host cells can then be used to create non-human transgenic animals in which exogenous nucleic acid sequences encoding a photosensitive protein have been introduced into their genome or homologous recombinant animals in which endogenous nucleic acid sequences encoding a photosensitive protein have been altered. Such animals are useful for studying the function and/or activity of a photosensitive protein and for identifying and/or evaluating modulators of a photosensitive protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous gene encoding a photosensitive protein has been altered by homologous recombination between the endogenous gene and an exogenous DNA molecule introduced into a cell of the animal, e.g., an embryonic cell of the animal, prior to development of the animal.

A transgenic animal of the invention can be created by introducing a photosensitive protein-encoding nucleic acid into the male pronuclei of a fertilized oocyte, e.g., by microinjection, retroviral infection, and allowing the oocyte to develop in a pseudopregnant female foster animal. The cDNA sequence of the photosensitive protein can be introduced as a transgene into the genome of a non-human animal. Alternatively, a nonhuman homologue of a human gene encoding a photosensitive protein can be used as a transgene. Intronic sequences and polyadenylation signals can also be included in the transgene to increase the efficiency of expression of the transgene. A cell-type specific regulatory sequence(s) can be operably linked to a transgene encoding a photosensitive protein to direct expression of the photosensitive protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a transgene encoding a photosensitive protein in its genome and/or expression of mRNA encoding a photosensitive protein in tissues or cells of the animals. A transgenic founder animal can then be used to breed additional animals carrying the transgene. Moreover, transgenic animals carrying a transgene encoding a photosensitive protein can further be bred to other transgenic animals carrying other transgenes.

To create a homologous recombinant animal, a vector is prepared which contains at least a portion of a gene encoding a photosensitive protein into which a deletion, addition or substitution has been introduced to thereby alter, e.g., functionally disrupt, the gene encoding the photosensitive protein. The gene encoding the photosensitive protein can be a human gene, but more preferably, is a non-human homologue of a human gene encoding a photosensitive protein. For example, a mouse gene encoding a photosensitive protein can be used to construct a homologous recombination nucleic acid molecule, e.g., a vector, suitable for altering an endogenous gene encoding a photosensitive protein in the mouse genome. In a preferred embodiment, the homologous recombination nucleic acid molecule is designed such that, upon homologous recombination, the endogenous gene encoding the photosensitive protein is functionally disrupted (i e., no longer encodes a functional protein; also referred to as a "knock out" vector). Alternatively, the homologous recombination nucleic acid molecule can be designed such that, upon homologous recombination, the endogenous gene encoding the photosensitive protein is mutated or otherwise altered but still encodes functional protein (e.g., the upstream regulatory region can be altered to thereby alter the expression of the endogenous protein encoding the photosensitive protein). In the homologous recombination nucleic acid molecule, the altered portion of the gene encoding the photosensitive protein is flanked at its 5' and 3' ends by additional nucleic acid sequence of the gene encoding the photosensitive protein to allow for homologous recombination to occur between the exogenous gene encoding the photosensitive protein carried by the homologous recombination nucleic acid molecule and an endogenous gene encoding the photosensitive protein in a cell, e.g., an embryonic stem cell. The additional flanking nucleic acid sequence encoding the photosensitive protein is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) Cell 51:503 for a description of homologous recombination vectors). The homologous recombination nucleic acid molecule is introduced into a cell, e.g., an embryonic stem cell line (e.g., by electroporation) and cells in which the introduced gene encoding the photosensitive protein has homologously recombined with the endogenous gene encoding the photosensitive protein are selected (see e.g., Li, E. et al. (1992) Cell 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

The nucleic acid encoding the photosensitive protein of interest can be administered to a retinal cell of a subject suffering from a photoreceptor cell degeneration disorder through any method known to one skilled in the art. In one embodiment, the nucleic acid encoding the photosensitive protein of interest is introduced to a subject through the use of a gene therapy vector. The nucleic acid molecule encoding the photosensitive protein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In one embodiment of the invention, the gene therapy vector is a viral vector, e.g. retrovirus, replication defective retrovirus, lentivirus, adenovirus, adeno-associated virus, herpesvirus, SV-40 virus, Epstein-Barr virus, or a pox virus, wherein the nucleic acid molecule encoding the photosensitive protein is ligated into the viral genome. Viral vectors, including lentiviruses, replication defective retroviruses, retrovirus, and adeno-associated virus vectors, are generally understood to be the gene therapy vector of choice for the transfer of exogenous genes in vivo, particularly into humans. These vectors provide efficient delivery of genes into cells, and the transferred nucleic acids are stably integrated into the chromosomal DNA of the host. A prerequisite for the use of lentiviruses and retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Protocols for producing recombinant retroviruses and for infecting cells in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include OA pZIP, pWE and pEM which are well known to those skilled in the art.

An adeno-associated virus (AAV) vector may also be used to treat the effects of photoreceptor cell degeneration in a subject in the methods of the present invention. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and are used to infect a wide variety of cell types. AAV is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). For example, the cDNA encoding human melanopsin may be inserted into an AAV gene therapy vector using standard molecular biology techniques.

The infectivity of the viral vector can be made cell-specific by expressing cell-specific proteins on the surface of the viral particle which will interact with receptors unique to the cell of interest. In this manner, the viral vector can be targeted to retinal ganglion cells. Expression is further enhanced by the use of tissue- or cell-specific transcriptional regulatory sequences which control expression of the gene.

The step of facilitating the production of infectious viral particles in the cells may be carried out using conventional techniques, such as standard cell culture growth techniques. The step of collecting the infectious virus particles can also be carried out using conventional techniques. For example, the infectious particles can be collected by cell lysis, or collection of the supernatant of the cell culture, as is known in the art. Optionally, the collected virus particles may be purified. Suitable purification techniques are well known to those skilled in the art. Alternatively, the viral vectors of the invention can be administered ex vivo or in vitro to cells or tissues using standard transfection techniques well known in the art.

Other methods relating to the use of viral vectors in gene therapy can be found in, e.g., Kay, M. A. (1997) *Chest* 111(6 Supp.):138S-142S; Ferry, N. and Heard, J. M. (1998) *Hum. Gene Ther.* 9:1975-81; Shiratory, Y. et al. (1999) *Liver* 19:265-74; Oka, K. et al. (2000) *Curr. Opin. Lipidol.* 11:179-86; Thule, P. M. and Liu, J. M. (2000) *Gene Ther.* 7:1744-52; Yang, N. S. (1992) *Crit. Rev. Biotechnol.* 12:335-56; Alt, M. (1995) *J. Hepatol.* 23:746-58; Brody, S. L. and Crystal, R. G. (1994) *Ann. N.Y. Acad. Sci.* 716:90-101; Strayer, D. S. (1999) *Expert Opin. Investig. Drugs* 8:2159-2172; Smith-Arica, J. R. and Bartlett, J. S. (2001) *Curr. Cardiol. Rep.* 3:43-49; and Lee, H. C. et al. (2000) *Nature* 408:483-8.

The vectors described herein can be administered in vivo to subjects by any suitable route, as is well known in the art. The term "administration" refers to the route of introduction of a formulated vector into the body. The vectors of the present invention can be delivered to the eye, and more specifically the retina, through a variety of routes. They may be delivered intraocularly, by topical application to the eye or by intraocular injection into, for example the vitreous or subretinal (interphotoreceptor) space. Alternatively, they may be delivered locally by insertion or injection into the tissue surrounding the eye. Alternatively, they may be delivered by means of a catheter or by means of an implant, wherein such an implant is made of a porous, non-porous or gelatinous material, including membranes such as silastic membranes or fibers, biodegradable polymers, or proteinaceous material.

The vectors may be delivered alone or in combination, and may be delivered along with a pharmaceutically acceptable vehicle. Ideally, such a vehicle would enhance the stability and/or delivery properties. The invention also provides for pharmaceutical compositions containing the active factor or fragment or derivative thereof, which can be administered using a suitable vehicle such as liposomes, microparticles or microcapsules. In various embodiments of the invention, it may be useful to use such compositions to achieve sustained release of the active component. The amount of vector to be administered in order to be effective in the treatment of a particular disorder or condition will depend on the nature of the disorder or condition and can be determined by standard clinical techniques.

Another aspect of the invention pertains to pharmaceutical compositions comprising the vectors of the invention. In one embodiment, the composition includes a vector in a therapeutically effective amount sufficient to treat photoreceptor cell degeneration, and a pharmaceutically acceptable carrier. A "therapeutically effective amount" refers to an amount effective, at dosages and for periods of time necessary, to achieve the desired therapeutic result, such as treatment of photoreceptor cell degeneration. A therapeutically effective amount of a vector may vary according to factors such as the disease state, age, sex, and weight of the individual, and the ability of the vector to elicit a desired response in the individual. Dosage regimens may be adjusted to provide the optimum therapeutic response. A therapeutically effective amount is also one in which any toxic or detrimental effects of the vector are outweighed by the therapeutically beneficial effects. The potential toxicity of the vector of the invention can be assayed using cell-based assays or art recognized animal models and a therapeutically effective modulator can be selected which does not exhibit significant toxicity. In a preferred embodiment, a therapeutically effective amount of a vector is sufficient to treat photoreceptor cell degeneration.

As used herein "pharmaceutically acceptable carrier" includes any and all solvents, dispersion media, coatings, antibacterial and antifungal agents, isotonic and absorption delaying agents, and the like that are physiologically compatible. Preferably, the carrier is suitable for administration directly into an affected eye. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Sterile injectable solutions can be prepared by incorporating a vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is to be noted that dosage values may vary with the severity of the condition to be alleviated. It is to be further understood that for any particular subject, specific dosage regimens can be adjusted over time according to the individual need and the professional judgment of the person administering or supervising the administration of the composition.

The amount of vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

This invention is further illustrated by the following examples which should not be construed as limiting. The contents of all references, patents and published patent applications cited throughout this application are incorporated herein by reference.

EXEMPLIFICATION

Example 1 Transgenic Expression of a Photosensitive Protein in Mice

The methods of the invention can be further implemented by creating a transgenic mouse which ectopically expresses photosensitive pigments with background containing a mutation which is characterized by a degenerative photoreceptor phenotype. First, a transgenic mouse which ectopically expresses photosensitive pigments in its retinal ganglion cells, or other non-photoreceptor cells in the retina, is created. This mouse is then crossed with a mouse containing a mutation which causes the degeneration of photoreceptor cells. The progeny of this cross will carry the photoreceptor degeneration mutation and the transgene that allows for ectopic expression of the photosensitive pigment. These transgenic mutant mice are then examined for restoration of their vision resulting from the ectopic expression of the photosensitive pigment protein.

A transgenic mouse which ectopically expresses melanopsin, or alternatively other vertebrate opsins or light-sensitive proteins, in retinal ganglion cells is created. This mouse is created using standard molecular biology techniques know in the art, described, for example, in U.S. Pat. Nos. 4,736,866 and 4,870,009 and Hogan, B. et al., (1986) A Laboratory Manual, Cold Spring Harbor, N.Y., Cold Spring Harbor Laboratory. Briefly, a nucleic acid molecule encoding the melanopsin protein is transferred into the male pronuclei of a fertilized oocyte of a mouse. This procedure may be performed by microinjection. The injected fertilized oocyte is then transferred to and develops in a pseudopregnant female foster mouse. After the birth of the litter, genotyping is performed on the pups, through standard techniques in the art, to determine the presence of the melanopsin transgene. Once a carrier mouse has been identified, a transgenic founder animal is used to breed additional animals carrying the transgene.

To restrict expression of the transgene to ganglion cells, the melanopsin gene is linked to a cell-type specific promoter, such as the promoter for thy-I. Alternatively, to express ectopic melanopsin in retinal rod bipolar cells, the promoter for the L7 gene is linked to the transgene. Also, intronic sequences and polyadenylation signals are included in the transgene to increase the efficiency of expression of the transgene.

For the second part of the experiment, a mutant mouse strain is chosen which exhibits photoreceptor degeneration due to a mutation. Many strains of mice exist in which the photoreceptor cells degenerate due to expression of a naturally occurring or genetically engineered mutation of proteins contained in the photoreceptor cells. For example, mouse strains exist in which there are mutations of rhodopsin, the beta subunit of cGMP phosphodiesterase, or the rod cGMP gated channel, which are all mutations that cause retinal degeneration in humans.

To analyze the effect of in vivo expression of the photosensitive protein melanopsin in mice that experience photoreceptor degeneration, the melanopsin transgenic mouse is crossed with the mouse from the mutant strain containing the photoreceptor mutation. Offspring from this cross are subsequently genotyped to identify a transgenic mutant, a carrier of both the debilitating mutation and the melanopsin transgene. Tests of the transgenic mutant's visual reflexes and/or vision are then carried out to determine whether or not ectopically expressed melanopsin can alleviate the visual disorder of mice containing the photoreceptor mutation. Expression of a light-sensitive pigment in the retinal ganglion cells should preserve some level of vision even after complete degeneration of the photoreceptor cells.

Example 2 Effects of Transgenic Expression of Photopigment Proteins in Non-Photoreceptor Cells of Mice Exhibiting Photoreceptor Cell Degeneration Mice in which the photoreceptor cells degenerate due to expression of a naturally occurring or genetically engineered mutation of proteins contained in the photoreceptor cells, are used for testing the effectiveness of gene therapy in correcting a visual disorder. Using commonly known techniques in molecular biology, gene therapy vectors are created that contain a photosensitive protein such as melanopsin. Visually impaired mice from mutant strains are selected based on their level of photoreceptor degeneracy. Gene therapy techniques are used to transfect the retinal ganglion cells of the selected mouse with a vector containing melanopsin. Tests to determine the mouse's visual reflexes and/or vision are then carried out to determine whether or not the ectopically expressed melanopsin can alleviate the visual disorder of mice containing the photoreceptor mutation. The overall function of the retina can be assessed electrophysiologically, by measuring, using conventional techniques, the responses of the retinal ganglion cells to light. A simple test of vision is the pupilary light reflex. Other tests include the Morris water maze and operantly conditioned discrimination between striped patterns.

Example 3 Gene Therapy Vector-Mediated Delivery of Melanopsin to Non-Photoreceptor Cells in Humans The gene encoding melanopsin is delivered to non-photoreceptor cells of a human subject suffering from a disorder characterized by photoreceptor cell degeneration, via a gene therapy vector according to the following procedure.

It is well known that transduction of appropriate target cells represents the first critical step in gene therapy, therefore choice of the particular gene delivery system will depend on factors such as the phenotype of the intended target, the route of administration and/or whether the transduction occurs in vivo or ex vivo. The nucleic acid molecule encoding the protein of interest is inserted into a gene therapy vector using methods commonly known in the art. Gene therapy vectors are delivered by various means, including intravenous injection, local administration (see U.S. Pat. No. 5,328,470) or by stereotactic injection (see, e.g., Chen et al. (1994) Proc. Natl. Acad. Sci. USA 91:3054-3057). Infection of retinal cells with the gene therapy vector allows a large proportion of non-photoreceptor cells to receive the melanopsin gene and subsequently express it. A pharmaceutical preparation of the gene therapy vector may comprise a gene therapy vector in an acceptable diluent, or comprise a slow release matrix in which the gene delivery vehicle is imbedded. Alternatively, the gene delivery vector is produced as a whole from recombinant cells, and the pharmaceutical preparation includes one or more cells which produce the gene delivery system.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for improving an eyesight of a subject suffering from age-related macular degeneration characterized by photoreceptor cell degeneration, consisting of injecting intraocularly a recombinant viral vector consisting essentially of a promoter operably linked to a nucleic acid encoding a single polypeptide, wherein said polypeptide is rhodopsin, into a non-photoreceptor retinal cell selected from the group consisting of horizontal cells, amacrine cells, bipolar cells, and ganglion cells of an affected eye of the subject suffering from age-related macular degeneration such that the eyesight of the subject is improved.

2. The method of claim 1, wherein the viral vector is selected from the group consisting of a retrovirus, a replication defective retrovirus, a lentivirus, an adenovirus, an adeno-associated virus, a herpesvirus, a SV-40 virus, an Epstein-Barr virus, and a pox virus.

3. The method of claim 1, wherein the promoter is a cell-type specific promoter.

4. The method of claim 1, wherein the intraocular injection is into the vitreous or sub-retinal space.

5. The method of claim 1, wherein the subject wears photosensitive corrective lenses.

* * * * *